(12) United States Patent
Martin et al.

(10) Patent No.: US 9,339,039 B1
(45) Date of Patent: May 17, 2016

(54) **INSECTICIDAL STRAINS OF *CHROMOBACTERIUM VACCINII* SP. NOV. FOR CONTROL OF INSECTS**

(71) Applicants: The United States of America, as Represented by the Secretary of Agriculture, Washington, DC (US); Midwestern University, Glendale, AZ (US)

(72) Inventors: Phyllis A. Martin, Lanham, MD (US); Scott Soby, Phoenix, AZ (US)

(73) Assignee: The United States of America, as Represented by Midwestern University, Washington, DC (US)

( * ) Notice: Subject to any disclaimer, the term of this patent is extended or adjusted under 35 U.S.C. 154(b) by 0 days.

(21) Appl. No.: 14/338,549

(22) Filed: Jul. 23, 2014

Related U.S. Application Data

(60) Provisional application No. 61/863,046, filed on Aug. 7, 2013.

(51) Int. Cl.
*A01N 63/00* (2006.01)
(52) U.S. Cl.
CPC ..................................... *A01N 63/00* (2013.01)
(58) Field of Classification Search
None
See application file for complete search history.

(56) References Cited

U.S. PATENT DOCUMENTS

2003/0068304 A1\* 4/2003 Mattingly ............ A01N 25/006
424/93.4

OTHER PUBLICATIONS

Soby, SD et al. *Chromobacterium vaccinii* sp. nov., isolated from native and cultivated cranberry (*Vaccinium macrocarpon* Ait.) bogs and irrigation ponds. International Journal of Systematic and Evolutionary Microbiology. 2013. 63: 1840-1846. Supplement included. Published online on Jan. 5, 2013.\*

\* cited by examiner

*Primary Examiner* — Renee Claytor
*Assistant Examiner* — Susan E Fernandez
(74) *Attorney, Agent, or Firm* — Jpon D. Fado; G. Byron Stover

(57) ABSTRACT

Disclosed are biocontrol agents for the control of insects (e.g., moths, and mosquitoes such as *Aedes aegypti*), in particular *Chromobacterium vaccinii* strains capable of killing insects such as mosquitoes and moths. More specifically, disclosed are *Chromobacterium vaccinii* strains MWU205 (NRRL B-50840), MWU300 (NRRL B-50841) and MWU328 (NRRL B-50842). Also disclosed is a biocontrol strategy whereby insects (e.g. mosquitoes, moths) are exposed to the *Chromobacterium vaccinii* strains MWU205, MWU300 or MWU328 as a method for killing insects, including insect larvae in more than one taxonomic order.

5 Claims, 9 Drawing Sheets
(2 of 9 Drawing Sheet(s) Filed in Color)

Phylogenetic tree of *Chromobacterium* isolates based on Matrix-assisted laser desorption/ionization time-of-flight mass spectroscopy (MALDI-TOF-MS).

SEQUENCE LISTING

<160> NUMBER OF SEQ ID NOS: 3

<210> SEQ ID NO 1
<211> LENGTH: 1528
<212> TYPE: DNA
<213> ORGANISM: Chromobacterium vaccinii

<400> SEQUENCE: 1

```
agagtttgat catggctcag attgaacgct ggcggcatgc tttacacatg caagtcgaac      60
ggtaacaggg tgcttgcacc gctgacgagt ggcgaacggg tgagtaatgc gtcggaatgt     120
accgtgtaat gggggatagc tcggcgaaag ccggattaat accgcatacg ccctgagggg     180
gaaagtgggg gaccgtaagg cctcacgtta tacgagcagc cgacgtctga ttagctagtt     240
ggtgaggtaa gagctcacca aggcgacgat cagtagcggg tctgagagga tgatccgcca     300
cactgggact gagacacggc ccagactcct acgggaggca gcagtgggga attttggaca     360
atgggcgcaa gcctgatcca gccatgccgc gtgtctgaag aaggccttcg ggttgtaaag     420 gactttgtt cgggaggaaa tcccgctggt taatacctgg cggggatgac agtaccggaa     480
gaataagcac cggctaacta cgtgccagca gccgcggtaa tacgtagggt gcaagcgtta     540
atcggaatta ctgggcgtaa agcgtgcgca ggcggttgtg caagtttgat tgaaagccc      600
```

```
cgggcttaac ctgggaacgg cattggagac tgcacgacta gagtgcgtca gagggggta      660
gaattccacg tgtagcagtg aaatgcgtag agatgtggag gaataccgat ggcgaaggca     720
gccccctggg atgacactga cgctcatgca cgaaagcgtg gggagcaaac aggattagat     780
accctggtag tccacgccct aaacgatgtc aactagctgt tggggggtttg aatccttggt   840
```
```
cgggcttaac ctgggaacgg cattggagac tgcacgacta gagtgcgtca gagggggta      660
gaattccacg tgtagcagtg aaatgcgtag agatgtggag gaataccgat ggcgaaggca     720
gccccctggg atgacactga cgctcatgca cgaaagcgtg gggagcaaac aggattagat     780
accctggtag tccacgccct aaacgatgtc aactagctgt tggggggtttg aatccttggt   840
agcgtagcta acgcgtgaag ttgaccgcct ggggagtacg gccgcaaggt taaaactcaa     900
aggaattgac ggggacccgc acaagcggtg gatgatgtgg attaattcga tgcaacgcga    960
aaaaccttac ctgctcttga catgtacgga acttggtaga gatatcttgg tgcccgaaag   1020
ggagccgtaa cacaggtgct gcatggctgt cgtcagctcg tgtcgtgaga tgttgggtta   1080
agtcccgcaa cgagcgcaac ccttgtcatt agttgccatc attaagttgg cactctaat    1140
gagactgccg gtgacaaacc ggaggaaggt ggggatgacg tcaagtcctc atggccctta   1200
tgagcagggc ttcacacgtc atacaatggt cggtacagag ggttgccaag ccgcgaggtg   1260
gagctaatct cagaaaaccg atcgtagtcc ggatcgcact ctgcaactcg agtgcgtgaa   1320
gtcggaatcg ctagtaatcg cagatcagca tgctgcggtg aatacgttcc cgggtcttgt   1380
acacaccgcc cgtcacacca tgggagtgag tttcaccaga agtgggtagg ctaaccgcaa   1440
ggaggccgct taccacggtg ggattcatga ctggggtgaa gtcgtaacaa ggtagccgta   1500
ggggaacctg cggctggatc acctcctt                                      1528
```

<210> SEQ ID NO 2
<211> LENGTH: 1528
<212> TYPE: DNA
<213> ORGANISM: Chromobacterium vaccinii

<400> SEQUENCE: 2

```
agagtttgat catggctcag attgaacgct ggcggcatgc tttacacatg caagtcgaac     60
ggtaacaggg tgcttgcacc gctgacgagt ggcgaacggg tgagtaatgc gtcggaatgt    120
accgtgtaat gggggatagc tcggcgaaag ccggattaat accgcatacg ccctgagggg    180
gaaagtgggg gaccgtaagg cctcacgtta tacgagcagc cgacgtctga ttagctagtt    240
ggtgaggtaa gagctcacca aggcgacgat cagtagcggg tctgagagga tgatccgcca    300
cactgggact gagacacggc ccagactcct acgggaggca gcagtgggga attttggaca    360
atgggcgcaa gcctgatcca gccatgccgc gtgtctgaag aaggccttcg ggttgtaaag    420
gacttttgtt cgggaggaaa tcccgctggt taatacctgg cggggatgac agtaccggaa    480
gaataagcac cggctaacta cgtgccagca gccgcggtaa tacgtagggt gcaagcgtta    540
atcggaatta ctgggcgtaa agcgtgcgca ggcggttgtg caagtctgat gtgaaagccc    600
cgggcttaac ctgggaacgg cattggagac tgcacgacta gagtgcgtca gagggggta     660
gaattccacg tgtagcagtg aaatgcgtag agatgtggag gaataccgat ggcgaaggca    720
gccccctggg atgacactga cgctcatgca cgaaagcgtg gggagcaaac aggattagat    780
accctggtag tccacgccct aaacgatgtc aactagctgt tggggggtttg aatccttggt   840
agcgtagcta acgcgtgaag ttgaccgcct ggggagtacg gccgcaaggt taaaactcaa    900
aggaattgac ggggacccgc acaagcggtg gatgatgtgg attaattcga tgcaacgcga    960
aaaaccttac ctgctcttga catgtacgga acttggtaga gatatcttgg tgcccgaaag   1020
ggagccgtaa cacaggtgct gcatggctgt cgtcagctcg tgtcgtgaga tgttgggtta   1080
agtcccgcaa cgagcgcaac ccttgtcatt agttgccatc attaagttgg cactctaat    1140
gagactgccg gtgacaaacc ggaggaaggt ggggatgacg tcaagtcctc atggccctta   1200
```

-continued

```
tgagcagggc ttcacacgtc atacagtggt cggtacagag ggttgccaag ccgcgaggtg    1260
gagctaatct cagaaaaccg atcgtagtcc ggatcgcact ctgcaactcg agtgcgtgaa    1320
gtcggaatcg ctagtaatcg cagatcagca tgctgcggtg aatacgttcc cgggtcttgt    1380
acacaccgcc cgtcacacca tgggagtgag tttcaccaga agtgggtagg ctaaccgcaa    1440
ggaggccgct taccacggtg ggattcatga ctggggtgaa gtcgtaacaa ggtagccgta    1500
ggggaacctg cggctggatc acctcctt                                       1528

<210> SEQ ID NO 3
<211> LENGTH: 1527
<212> TYPE: DNA
<213> ORGANISM: Chromobacterium vaccinii

<400> SEQUENCE: 3
agagtttgat catggctcag attgaacgct ggcggcatgc tttacacatg caagtcgaac      60
ggtaacaggg tgcttgcacc gctgacgagt ggcgaacggg tgagtaatgc gtcggaatgt     120
accgtgtaat gggggatagc tcggcgaaag ccggattaat accgcatacg ccctgagggg     180
gaaagtgggg gaccgtaagg cctcacgtta tacgagcagc cgacgtctga ttagctagtt     240
ggtgaggtaa gagctcacca aggcgacgat cagtagcggg tctgagagga tgatccgcca     300
cactgggact gagacacggc ccagactcct acgggaggca gcagtgggga attttggaca     360
atgggcgcaa gcctgatcca gccatgccgc gtgtctgaag aaggccttcg ggttgtaaag     420
gacttttgtt cgggaggaaa tcccgctggt taatacctgg cggggatgac agtaccggaa     480
gaataagcac cggctaacta cgtgccagca gccgcggtaa tacgtagggt gcaagcgtta     540
atcggaatta ctgggcgtaa agcgtgcgca ggcggttgtg taagtctgat gtgaaagccc     600
cgggcttaac ctgggaacgg cattggagac tgcacgacta gagtgcgtca ggggggta      660 gaattccacg tgtagcagtg aaatgcgtag agatgtggag gaataccgat ggcgaaggag     720
ccccctggga tgacactgac gctcatgcac gaaagcgtgg ggagcaaaca ggattagata     780
ccctggtagt ccacgcccta aacgatgtca actagctgtt ggggtttga atccttggta     840 gcgtagctaa cgcgtgaagt tgaccgcctg gggagtacgg ccgcaaggtt aaaactcaaa     900
ggaattgacg gggacccgca caagcggtgg atgatgtgga ttaattcgat gcaacgcgaa     960
aatccttacc tgctcttgac atgtacgaa cttggtagag atatcttggt gcccgaaagg    1020
gagccgtaac acaggtgctg catggctgtc gtcagctcgt gtcgtgagat gttgggttaa    1080
gtcccgcaac gagcgcaacc cttgtcatta gttgccatca ttaagttggg cactctaatg    1140
agactgccgg tgacaaaccg gaggaaggtg gggatgacgt caagtcctca tggcccttat    1200
gagcagggct tcacacgtca tacaatggtc ggtacagagg gttgccaagc cgcgaggtgg    1260
agctaatctc agaaaaccga tcgtagtccg gatcgcactc tgcaactcga gtgcgtgaag    1320
tcggaatcgc tagtaatcgc agatcagcat gctgcggtga atacgttccc gggtcttgta    1380
cacaccgccc gtcacaccat gggagtgagt ttcaccagaa gtgggtaggc taaccgcaag    1440
gaggccgctt accacggtgg gattcatgac tggggtgaag tcgtaacaag gtagccgtag    1500
gggaacctgc ggctggatca cctcctt                                        1527
```

US 9,339,039 B1

INSECTICIDAL STRAINS OF *CHROMOBACTERIUM VACCINII* SP. NOV. FOR CONTROL OF INSECTS

REFERENCE TO RELATED APPLICATION

This application claims the benefit of U.S. Provisional Application No. 61/863,046, filed 7 Aug. 2013, which is incorporated herein by reference in its entirety.

BACKGROUND OF THE INVENTION

Disclosed are biocontrol agents for the control of insects (e.g., moths and mosquitoes such as *Aedes aegypti*), in particular *Chromobacterium vaccinii* strains capable of killing insects such as mosquitoes and moths. More specifically, disclosed are *Chromobacterium vaccinii* strains MWU205 (NRRL B-50840), MWU300 (NRRL B-50841) and MWU328 (NRRL B-50842). Also disclosed are biocontrol strategies whereby insects (e.g. mosquitoes, moths) are exposed to the *Chromobacterium vaccinii* strains MWU205, MWU300 or MWU328 as a method for killing insects, including insect larvae in more than one taxonomic order.

After the discovery of a new species of *Chromobacterium, C. subtsugae*, that killed insects (Martin, P. A. W., et al., International Journal of Systematic and Evolutionary Microbiology, 57: 993-999 (2007); U.S. Pat. No. 7,244,607), we tested other chromobacteria for insecticidal activity. In the case of *C. violaceum*, the type strain of this species (ATCC 12472$^T$) was not toxic to several species of insects (e.g. Colorado potato beetle, diamondback moth, southern corn rootworm) whereas *C. subtsugae* was toxic. *C. subtsugae*, although it kills a variety of insects, was not effective against mosquito larvae at similar concentrations and short time frames (16 h) compared to the 'gold standard' bacterial strain *Bacillus thuringiensis* var. *israelensis* (Bti; IBL 10003). Bti is an effective control agent of mosquitoes and black flies (Goldberg, L. J., and J. Margalit, Journal of the American Mosquito Control Association, 37: 355-358 (1977)) over the 30 years it has been in use. More recently resistance to the Cry toxin of Bti has been described in both *Lepidoptera* (moths) and *Aedes* mosquitoes (Cancino-Rodenzo et al., Insect Biochem. Mol. Biol., 40: 58-63 (2010)). Another sporeforming bacterium (*Lysinobacillus sphaericus*) also negatively affects mosquito larvae (Davidson, E. W., Mosq. News, 44: 147 (1984)) but no non-sporeforming bacteria are known to do so. Additionally, reliance on a single mode type of bacteria (i.e., Bti) is not the best long-term strategy for insect control because of the emergence of Bt resistance, and particularly in cases like mosquito control where it may not be possible or desirable to incorporate insect 'refuges' (Tabashnik, B. E., et al., J. Econ. Entomol., 96(4): 1031-8 (2003)).

With 219 million annual cases of malaria, over 100 million annual cases of dengue hemorrhagic fever, 200,000 cases of yellow fever, and millions of cases of other mosquito-borne infectious and parasitic diseases such as West Nile and chikungunya, coupled with insect resistance to chemical insecticides, there is a critical and global need for new biocontrol agents for insects such as mosquitoes.

SUMMARY OF THE INVENTION

Biocontrol agents for the control of insects (e.g., moths, and mosquitoes such as *Aedes aegypti*), in particular *Chromobacterium vaccinii* strains capable of killing insects such as mosquitoes and moths are described. More specifically, disclosed are *Chromobacterium vaccinii* strains MWU205 (NRRL B-50840), MWU300 (NRRL B-50841) and MWU328 (NRRL B-50842). Also disclosed are biocontrol strategies whereby insects (e.g. mosquitoes, moths) are exposed to the *Chromobacterium vaccinii* strains MWU205, MWU300 or MWU328 as a method for killing insects, including insect larvae in more than one taxonomic order.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

Deposit of the Microorganisms

*Chromobacterium vaccinii* strains MWU205 (NRRL B-50840), MWU300 (NRRL B-50841) and MWU328 (NRRL B-50842) have been deposited on Jun. 3, 2013 under the provisions of the Budapest Treaty, with U.S.D.A. Agricultural Research Service Patent Culture Collection (National Center for Agricultural Utilization Research, 1815 N. University Street, Peoria, Ill. 61604).

Thus a deposit of *Chromobacterium vaccinii* strains MWU205 (NRRL B-50840), MWU300 (NRRL B-50841) and MWU328 (NRRL B-50842) has been made in a depository affording permanence of the deposit and ready accessibility thereto by the public if a patent is granted. The depository is U.S.D.A. Agricultural Research Service Patent Culture Collection (National Center for Agricultural Utilization Research, 1815 N. University Street, Peoria, Ill. 61604). All restrictions on the availability to the public of the materials so deposited will be irrevocably removed upon the granting of a patent. The materials have been deposited under conditions that access to the materials will be available during the pendency of the patent application to one determined by the Commissioner to be entitled thereto under 37 CFR Section 1.14 and 35 U.S.C Section 122. The deposited materials will be maintained with all the care necessary to keep it viable and uncontaminated for a period of at least five years after the most recent request for the furnishing of a sample of the deposited microorganisms, and in any case, for a period of at least thirty (30) years after the date of deposit for the enforceable life of the patent, whichever period is longer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SEQUENCE LISTING

Figure 1:
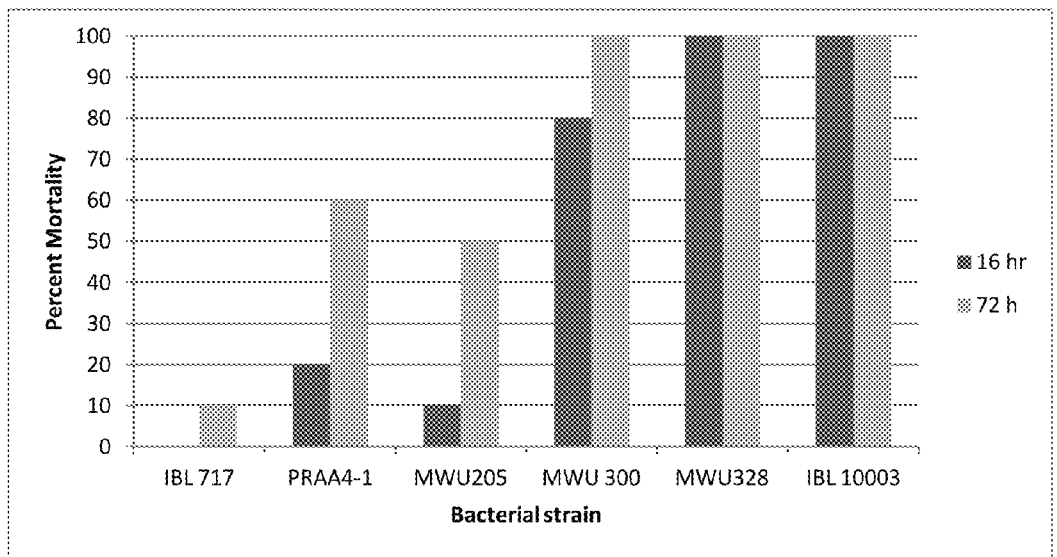
FIG. 1 is a comparison of three *Chromobacterium vaccinium* isolates (MWU205, MWU300 and MWU328) with *C. subtsugae* type strain PRAA4-1, and *Bacillus thuringiensis* isolates IBL 717 (negative control) and IBL 10003 (positive control), the 'gold standard' for insecticidal activity, on *Aedes aegypti* larvae six days after hatching as described below.
Figure 2:
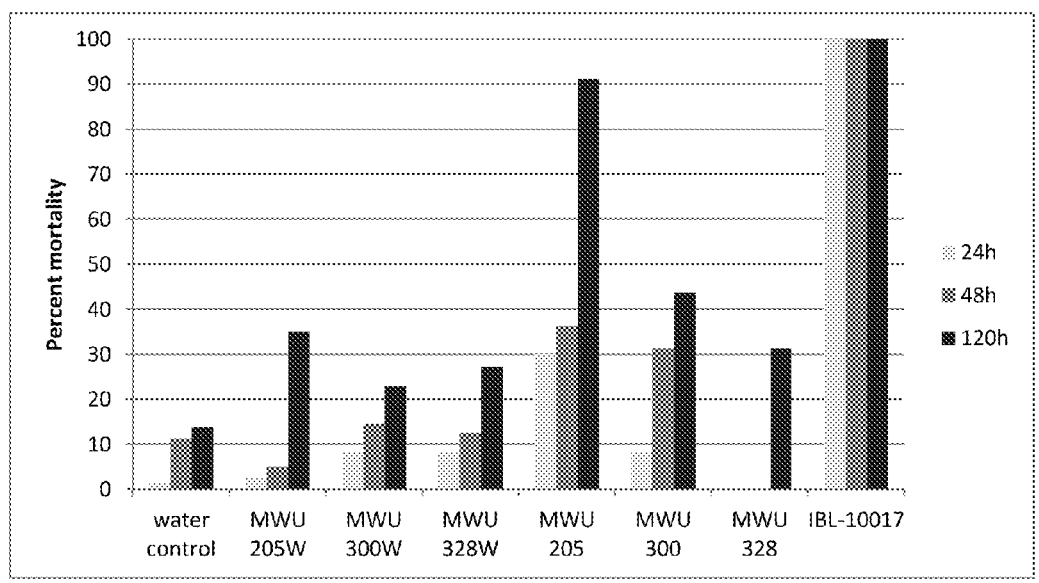
FIG. 2 shows the activity of MWU205 on Diamondback moth larvae, IBL-10017 is a *B. thuringiensis* strain included as a positive control as described below.
Figure 3:
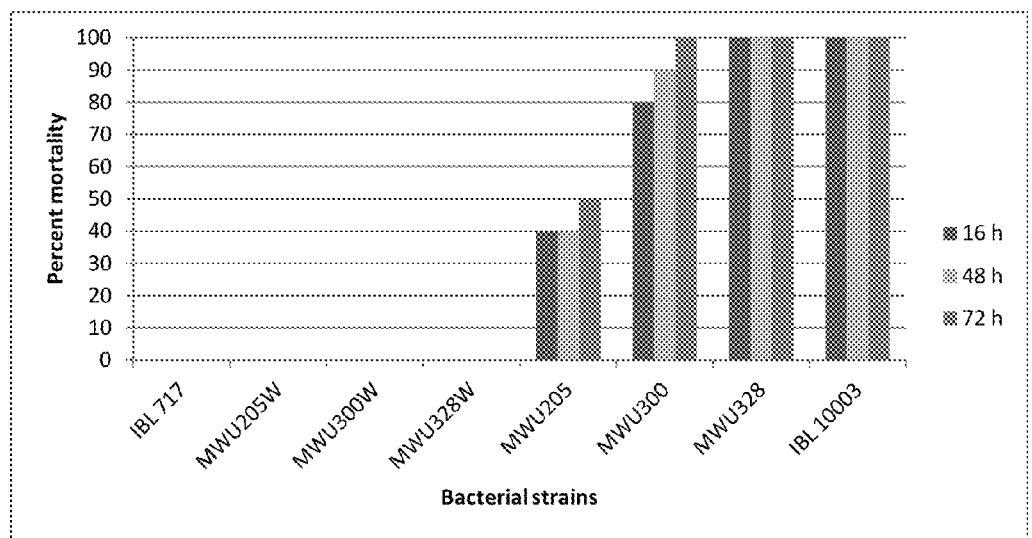
FIG. 3 shows a comparison of three *Chromobacterium vaccinium* isolates (MWU205, MWU300 and MWU328) with their cognate pigment-deficient mutants (MWU205W, MWU300W and MWU328W) for insecticidal activity on *Aedes aegypti* larvae six days after hatching (*B. thuringiensis* isolates were used as negative and positive controls) as described below.
Figure 4:
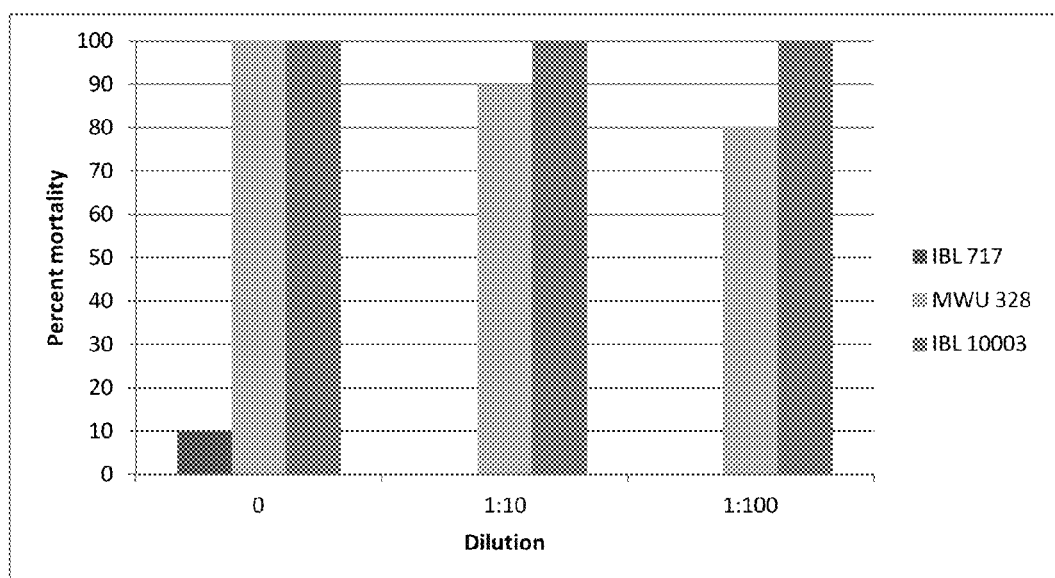
FIG. 4 shows toxicity of ten-fold dilutions of MWU328 compared to IBL 717 and IBL 10003 at 16 h post inoculation as described below.

Any nucleic acid and amino acid sequences listed herein or in the accompanying sequence listing are shown using standard letter abbreviations for nucleotide bases, and three letter code for amino acids, as defined in 37 C.F.R. Section 1.822. In at least some cases, only one strand of each nucleic acid sequence is shown, but the complementary strand is understood as included by any reference to the displayed strand.

SEQ ID NO: 1 shows the 16S rRNA sequence for MWU205 accession number JN120869.1.

SEQ ID NO: 2 shows the 16S rRNA sequence for MWU328 accession number JN120870.1.

SEQ ID NO: 2 shows the 16S rRNA sequence for MWU300 accession number JN117594.

DETAILED DESCRIPTION OF THE INVENTION

We have identified *C. vaccinii* strains MWU205 (NRRL B-50840), MWU300 (NRRL B-50841) and MWU328 (NRRL B-50842) that kill insects such as mosquitoes.

Disclosed are methods of killing insects, involving exposing (or treating) insects or an object (e.g. insects, plants, fruit trees, screens and netting, traps) or area (e.g. water, soil, house, farm land) in need of such treatment with an insect-killing effective amount of *C. vaccinii* strains MWU205, MWU300 or MWU328, and optionally a carrier. The terms "object" or "area" as used herein include any place where the presence of target pests is not desirable, including any type of tree, crop, natural or artificial parkland, watercourse, or other target pest habitat. The amount of the compositions used will be at least an effective amount. The term "effective amount," as used herein, means the minimum amount of the compositions needed to kill the insects when compared to the same area or object which is untreated. The precise amount needed will by necessity vary in accordance with the target insect; particular composition used; the type of area or object to be treated; weather or climatic conditions under which it is applied, and the environment in which the area or object is located. The precise amount of the composition can easily be determined by one skilled in the art given the teaching of this application. For example, one skilled in the art could follow the procedures utilized below; the composition would be statistically significant in comparison to a negative control. The composition may or may not contain a control agent for insects, such as an insecticide known in the art to kill insects. Other compounds (e.g. insect attractants, adjuvants, pheromones, adhesives, dispersants or biocontrol agents known in the art) may be added to the composition provided they do not substantially interfere with the intended activity or efficacy of the composition; whether or not a compound interferes with activity and/or efficacy can be determined, for example, by the procedures utilised below.

The carrier may be, for example, agronomically or physiologically or pharmaceutically acceptable carriers. The carrier as used herein is defined as not including the body of an insect (e.g. mosquitoes).

A single application will suffice under optimum conditions, with mortality occurring rapidly, but under suboptimum conditions, either higher concentrations or multiple applications may be necessary.

Herein an insect biocontrol composition refers to a microbial preparation wherein the microbes comprise, consist essentially of, or consist of *C. vaccinii* strains MWU205, MWU300 or MWU328. The insect biocontrol composition includes *C. vaccinii* strains MWU205, MWU300 or MWU328 on agriculturally acceptable carriers (e.g. insect food) which may be any carrier to which the *C. vaccinii* strains can be attached and are not harmful to plants or other non-target organisms which are treated with the composition.

We have found that the *C. vaccinii* strains that are especially useful possess the identifying characteristics of *C. vaccinii*. These characteristics include the following: (1) the ability to kill insects such as *Aedes* spp. or *Plutella* spp.; (2) DNA-DNA hybridization with *C. violaceum* ATCC12472 of 44.2% and with *C. subtsugae* PRAA4-1 of 28.0% (internationally-accepted criterion for speciation is ≤70%); (3) positive for oxidase, catalase, motility, arginine dyhydrolase; (4) negative for indole production, glucose fermentation, and production of urease, β-glucosidase, and β-galactosidase; (5)

assimilate D-glucose, N-acetylglucosamine, gluconate, capric acid and malic acid; (6) does not assimilate L-arabinose, D-mannitol, maltose or phenylacetic acid; (7) resistance to ampicillin and penicillin; (8) has a growth temperature optimum of 25°-26° C.; (9) production of pigment A (violacein) which is exported into planktonic growth medium but not solid medium and is produced at temperatures between 26° and 37° C. in King's Medium B, spectral properties of pigment A: peak at 585 nm, pigment B is a complex of dark brown compounds that include iron-chelating siderophores, are water soluble and diffuse into planktonic and solid media; (10) predominant fatty acid composition: C16:1ω7c, C16:1ω5c, C18:1ω5c, C14:1ω5c present but absent from *C. subtsugae* PRAA4-1 and *C. violaceum*, C15:0 absent but present in *C. subtsugae* PRAA4-1 and *C. violaceum*, C17:1ω5c absent but present in *C. subtsugae* PRAA4-1, C18:0 present but absent from *C. subtsugae* PRAA4-1; (11) grows in 3% NaCl (*C. subtsugae* PRAA4-1 and *C. violaceum* inhibited); (12) is a gram-negative facultative aerobe, motile rod producing a single polar flagellum, averaging 1.19 μm×3.03 μm, capable of growth between 4° C. and 40° C., grows on King's Medium B agar (20% proteose peptone #3, 1.5% $K_2HPO_4$, 1.5% $MgSO_4.7H_2O$, 10% glycerol, 1% agar) producing circular, smooth, convex glossy colonies starting out as cream-colored but rapidly becoming dark purple with purple pigment produced first in the center of the colony. Colonies do not fluoresce under long- or short-wave UV irradiation. See also the identifying characteristics in Table 1

We have found that the *C. vaccinii* isolates especially useful are strains possessing the identifying characteristics of *C. vaccinii* strains MWU205, MWU300, and MWU328.

Figure 5:
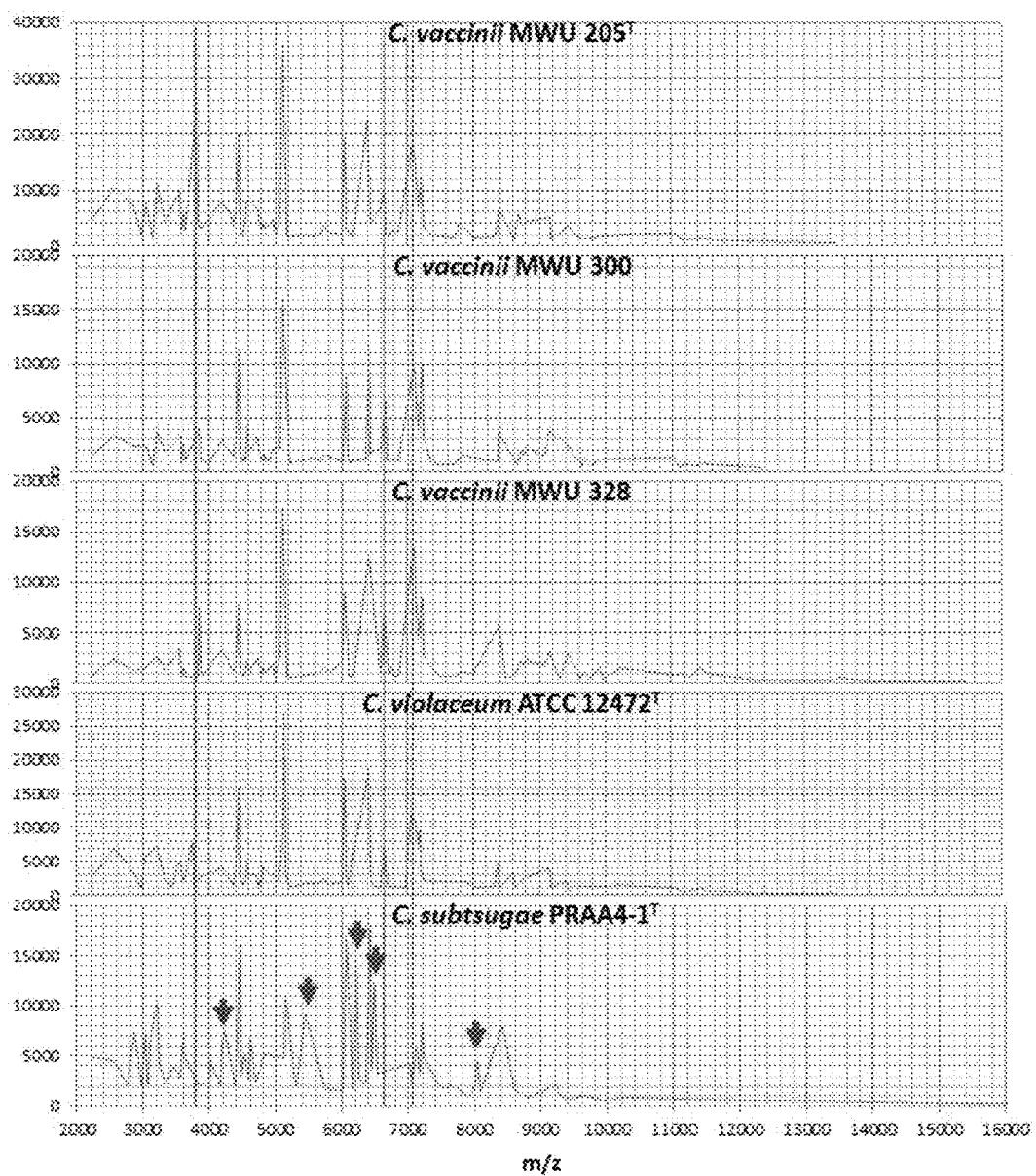
FIG. 5 shows Matrix-Assisted Laser Desorption/Ionization of Time-of-Flight Mass spectroscopy (MALDI-TOF-MS) analysis of *Chromobacterium* isolates as described below. Mid-log phase bacteria were harvested, washed with sterile water and resuspended in ethanol. Proteins were extracted with formic acid and spotted on a high-polish MALDI target. Protein peaks present in *C. violaceum* and *C. vaccinii* strains but absent from *C. subtsugae* are indicated with vertical green lines, and the five unique *C. subtsugae* peaks are indicated by red arrows.
Figure 6:
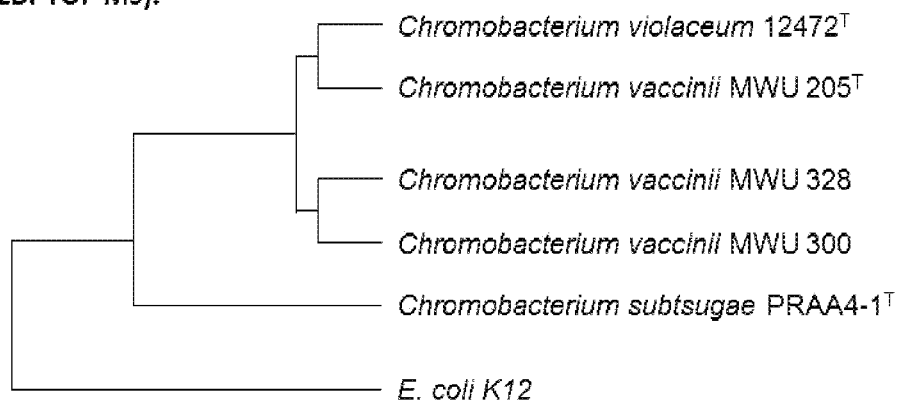
FIG. 6 shows a phylogenetic tree that was constructed using a distance matrix formed from MALDI-TOF-MS peak positions (m/z) and intensity (integration of peak area) of soluble proteins extracted from *C. violaceum, C. subtsugae,* and *C. vaccinii* as described below. Comparisons are based on the Unweighted Pair Group Method with Arithmetic Averages (UPGMA) as described below. *C. vaccinii* MWU328 and MWU300 (the mosquito-active isolates) form a separate subclade from *C. violaceum* and *C. vaccinii* MWU205. *C. subtsugae* is evolutionarily basal to the other *Chromobacterium* taxa, forming its own Glade. *E. coli* K12 is shown as the outgroup.
Figure 7:
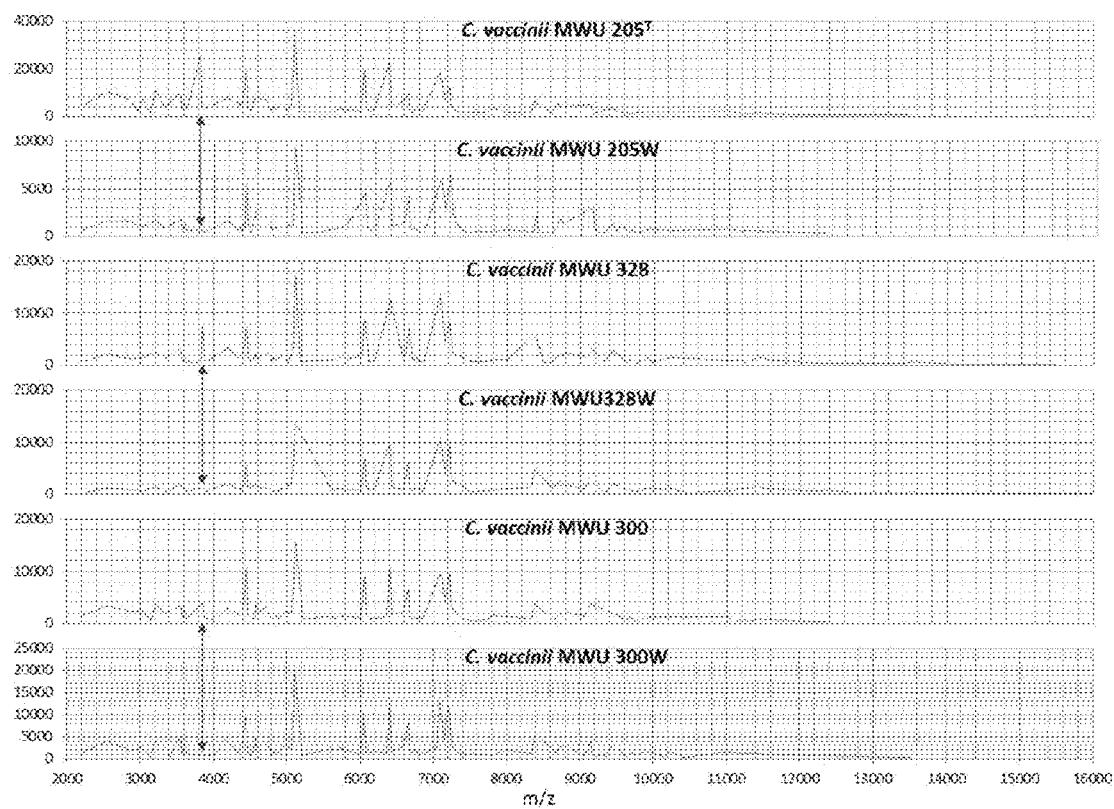
FIG. 7 shows Matrix-Assisted Laser Desorption/Ionization of Time-of-Flight Mass spectroscopy (MALDI-TOF-MS) analysis of wild type *Chromobacterium* isolates and their cognate violacein-deficient mutants as described below. Mid-log phase bacteria were harvested, washed with sterile water and resuspended in ethanol. Proteins were extracted with formic acid and spotted on a high-polish MALDI target. Protein peaks present in wild type *C. vaccinii* strains at 3818 m/z but absent from white mutants are indicated with red arrows.
Figure 8:
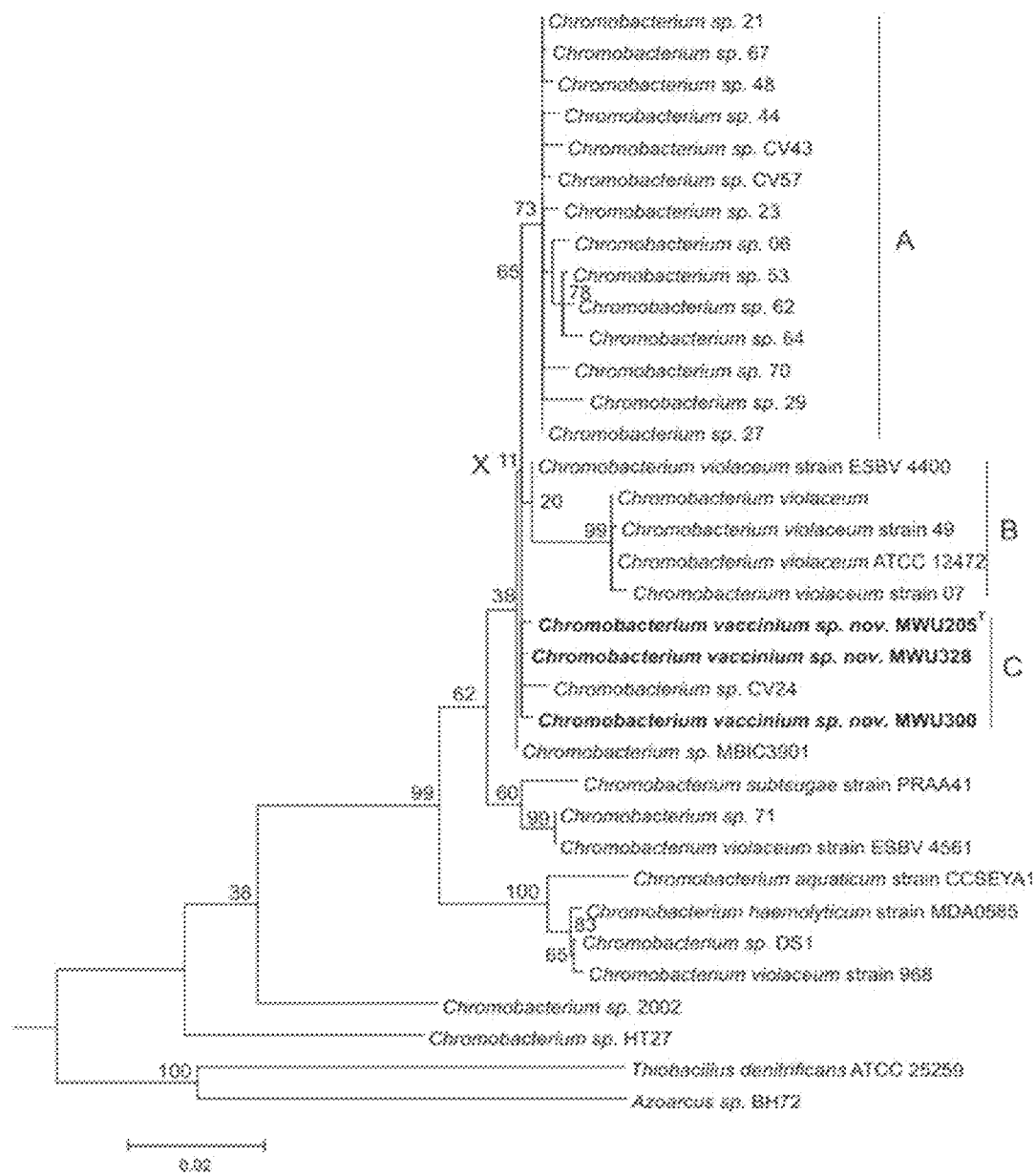
FIG. 8 shows maximum likelihood phylogenetic tree showing the evolutionary position of the MWU isolates (*Chromobacterium vaccinii* sp. nov.) in relation to *Chromobacterium* spp., *Thiobacillus denitrificans* ATCC 25259$^T$ and *Azoarcus* sp. BH72, and two other betaproteobacteria as outgroups as described below. Thirty-seven16S rRNA sequences from every *Chromobacterium* spp. GenBank accession meeting stringent length requirements (1371 bp) were aligned using MUSCLE and a tree was constructed using the Maximum Likelihood method (MEGA5). All bootstrap values, based on 500 replications, are shown at the nodes. Notably, *C. vaccinii, C. subtsugae,* and *C. violaceum* form clearly distinct clades (taxonomic groups), which are also separate from other *Chromobacterium* species.

These characteristics for MWU205 include the following: Cells are Gram-negative, aerobic, rod-shaped with mean dimensions (mean±sd) of 3.03 μm±0.555×1.19 μm±0.0198 (2.01 to 3.91 μm x 0.96 to 1.78 μm) having the MALDI-TOF-MS protein spectrum as in FIG. 5. A single, relatively short (4.91 μm±0.730; 3.14 to 6.12 μm) polar flagellum is produced. Colonies grow well on KMB and LB media, and are inherently resistant to penicillin and ampicillin at 50 μg $ml^{-1}$. Optimum growth occurs at 25°-26° C., growing up to 43° C. on KMB, producing round, smooth, glossy, convex colonies within 48 h, starting out as cream-colored and rapidly turning deep purple starting from the center of the colony. Violacein production is somewhat less at 37° C. and is absent at 43° C. Produces violacein-deficient mutants at high frequency particularly when grown on high salt concentration media. Cells grow freely in 2% (w/v) NaCl, and marginally in 3% (w/v) NaCl. Major fatty acids are $C_{16:1}ω7cis$ (41.94%), $C_{16:0}$ (29.56%) and $C_{18:1ω7cis}$ (12.63%). Colonies do not fluoresce under either short or long wave UV irradiation, but produce large amounts of the pigments violacein and deoxyviolacein at up to 37° C., eventually also producing a water-soluble brown pigment which diffuses freely in the medium. Positive for catalase and oxidase, produces arginine dihydrolase and β-galactosidase, and assimilates D-glucose, N-acetylglucosamine, gluconate, citrate, capric acid and malic acid, but is negative for glucose fermentation, urease and β-glucosidase. Does not produce indole from tryptophan, or assimilate L-arabinose, D-mannitol, maltose or phenylacetic acid. Secretes $7.9×10^{-6}$ ng violacein per cell and produces $1.3×10^{-6}$ ng intracellular violacein per cell when grown on KMB with aeration. Produces water-soluble brown pigment either on solid media or in planktonic culture. Active against diamondback moth (*Plutella xylostella*) larvae but not mosquito larvae at 16 h post hatch.

These characteristics for MWU300 include the following: Cells are Gram-negative, aerobic, rod-shaped with mean dimensions (mean±sd) of 3.03 μm±0.555×1.19 μm±0.0198 (2.01 to 3.91 μm x 0.96 to 1.78 μm) having the MALDI-TOF-MS protein spectrum as in FIG. 5. A single, relatively short (4.91 μm±0.730; 3.14 to 6.12 μm) polar flagellum is produced. Colonies grow well on KMB and LB media, and are inherently resistant to penicillin and ampicillin at 50 μg $ml^{-1}$. Optimum growth occurs at 25°-26° C., growing up to 43° C. on KMB, producing round, smooth, glossy, convex colonies within 48 h, starting out as cream-colored and rapidly turning deep purple starting from the center of the colony. Violacein production is somewhat less at 37° C. and is absent at 43° C. Produces violacein-deficient mutants at high frequency particularly when grown on high salt concentration media. Cells grow freely in 2% (w/v) NaCl, and marginally in 3% (w/v) NaCl. Major fatty acids are $C_{16:1}ω7cis$ (42.72%), $C_{16:0}$ (28.40%) and $C_{18:1ω7cis}$ (13.11%). Colonies do not fluoresce under either short or long wave UV irradiation, but produce large amounts of the pigments violacein and deoxyviolacein at up to 37° C. Positive for catalase and oxidase, produces arginine dihydrolase and β-galactosidase, and assimilates D-glucose, N-acetylglucosamine, gluconate, citrate, capric acid and malic acid, but is negative for glucose fermentation, urease and β-glucosidase. Does not produce indole from tryptophan, or assimilate L-arabinose, D-mannitol, maltose or phenylacetic acid. Secretes $3.4×10^{-6}$ ng violacein per cell and produces $6.4×10^{-7}$ ng intracellular violacein per cell when grown on KMB with aeration. Produces water-soluble brown pigment either on solid media or in planktonic culture. Active against mosquito larvae but not diamondback moth larvae.

These characteristics for MWU328 include the following: Cells are Gram-negative, aerobic, rod-shaped with mean dimensions (mean±sd) of 3.03 μm±0.555×1.19 μm±0.0198 (2.01 to 3.91 μm×0.96 to 1.78 μm) having the MALDI-TOF-MS protein spectrum as in FIG. 5. A single, relatively short (4.91 μm±0.730; 3.14 to 6.12 μm) polar flagellum is produced. Colonies grow well on KMB and LB media, and are inherently resistant to penicillin and ampicillin at 50 μg $ml^{-1}$. Optimum growth occurs at 25°-26° C., growing up to 43° C. on KMB, producing round, smooth, glossy, convex colonies within 48 h, starting out as cream-colored and rapidly turning deep purple starting from the center of the colony. Violacein production is somewhat less at 37° C. and is absent at 43° C. Produces violacein-deficient mutants at high frequency particularly when grown on high salt concentration media. Cells grow freely in 2% (w/v) NaCl, and marginally in 3% (w/v) NaCl. Colonies do not fluoresce under either short or long wave UV irradiation, but produce large amounts of the pigments violacein and deoxyviolacein at up to 37° C., eventually producing a water-soluble brown pigment which diffuses freely in the medium. Positive for catalase and oxidase, produces arginine dihydrolase and β-galactosidase, and assimilates D-glucose, N-acetylglucosamine, gluconate, citrate, capric acid and malic acid, but is negative for glucose fermentation, urease and β-glucosidase. Does not produce indole from tryptophan, or assimilate L-arabinose, D-mannitol, maltose or phenylacetic acid. Secretes $2.5×10^{-6}$ ng violacein per cell and produces $4.4×10^{-7}$ ng intracellular violacein per cell when grown on KMB with aeration. Active against mosquito larvae but not diamondback moth larvae.

The terms "object" or "area" as used herein include any place where the presence of target pests (e.g., mosquitoes) is not desirable, including any type of premises, which can be out-of-doors, such as in gardens, lawns, tents, camping bed nets, camping areas, farmland, parks, and so forth, or indoors, such as in barns, garages, commercial buildings, homes, and so forth, or any area where pests are a problem, such as in shipping or storage containers (e.g. bags, boxes, crates, etc.), packing materials, bedding, and so forth; also includes the outer covering of a living being, such as skin, fur, hair, or clothing. Thus the methods include dispensing the compounds or agents described herein into the environment in traps, sprays, emulsions, freeze-dried blocks, coatings or vapor form (e.g. an aerosol) preferably using devices that allow a slow sustained release of these compounds or agents into the environment from a sealed canister or chemical or physical (e.g. fabric) matrix.

The bacteria and compositions containing the bacteria can also be used for killing members of the Diptera order (e.g., *Aedes aegyti*) and the *Lepidoptera* order (e.g., diamondback moth). The bacteria and compositions containing the bacteria can also be used for killing harmful or troublesome bloodsucking and biting insects, ticks and mites including mosquitoes (for example *Aedes, Culex* and *Anopheles* species including but not limited to Tiger mosquitoes, *Aedes aboriginis, Aedes aegypti, Aedes albopictus, Aedes cantator, Aedes sierrensis, Aedes sollicitans, Aedes squamiger, Aedes sticticus, Aedes vexans, Anopheles quadrimaculatus, Culex pipiens,* and *Culex quinquefasciatus*), sand flies (for example *Phlebotomus* and *Lutzomyia* species), bed bugs (for example *Cimex lectularius*), owl gnats (*Phlebotoma*), blackfly (*Culicoides* species), buffalo gnats (*Simulium* species), biting flies (for example *Stomoxys calcitrans*), tsetse flies (*Glossina* species), horseflies (*Tabanus, Haematopota* and *Chrysops* species), house flies (for example *Musca domestica* and *Fannia canicularis*), meat flies (for example *Sarcophaga carnaria*), flies which cause myiasis (for example *Lucilia cuprina, Chrysomyia chloropyga, Hypoderma bovis, Hypoderma lineatum, Dermatobia hominis, Oestrus ovis, Gasterophilus intestinalis* and *Cochliomyia hominovorax*), bugs (for example *Cimex lectularius, Rhodnius prolixus* and *Triatoma infestans*), lice (for example *Pediculus humanus, Haematopinus suis* and *Damalina ovis*), louse flies (for example s), and fleas (for example *Pulex irritans, Cthenocephalides canis* and *Xenopsylla cheopis*), sand fleas (for example *Dermatophilus penetrans*), and blood-feeding ticks include (for example, *Ornithodorus moubata, Ixodes ricinus, Ixodes scapularis, Boophilus microplus, Amblyomma americanum,* and *Amblyomma hebreum, Dermacentor variabilis*) and mites (including for example, *Sarcoptes scabiei* and *Dermanyssus gallinae*).

The bacteria are preferably used in combination with one or more optional carriers or additives such as water, humectants, inert carriers, other insecticides, and colorants; typical humectants, inert carriers, insecticides, and colorants are well known in the art. As a practical matter, it is expected that the bacteria will be formulated with an inert carrier for use as a pesticide composition. Such inert carriers are well known in the art. Water is a particularly preferred carrier, although other inert carriers suitable for use herein include but are not limited to inorganic or organic biological buffers, alcohols, ethers, glycols, ketones, esters, and solid carriers such as clays, silicas, cellulosics, rubber, or synthetic polymers. Although water is generally preferred for use herein, other inert carriers are also suitable, and may even be preferred for example, when using non-water soluble insecticides, colorants, or other additives.

In another preferred embodiment, the bacteria are provided in combination with another insecticide effective for controlling the population of the targeted pest population. As used herein, the term "insecticide" refers to a material or mixture of materials which induce mortality, disrupt or impede growth, interfere with metamorphosis or other morphogenic functions, effect sterilization, or interfere with feeding, metabolism, respiration, locomotion or reproduction of the targeted insects (e.g. mosquitoes). Suitable insecticides include but are not limited to biological controls such as insect growth regulators, and materials that are toxic to insects (i.e. toxicants) such as chemical insecticides, pathogenic nematodes, fungi, protozoans, or other bacteria. Preferred insecticides are slow-acting (i.e. acting over a course of hours, days, weeks, or preferably months), to reduce "avoidance" effects before individuals have distributed the toxicant to other members of the population or colony. A variety of slow-acting insecticides are known in the art. In addition, otherwise faster-acting insecticides may act more slowly and used. Biological control agents that may be used as insecticides include toxins derived from biological control agents such as *B. thuringiensis* toxin.

The pesticidal compositions containing the bacteria described herein may, for example, be formulated as wettable powders, dusts, granules, adherent dusts or granules, solutions, emulsifiable concentrates, emulsions, suspension concentrates, aerosols, and baits. Optionally, the compounds may be further formulated with insect attractants such as pheromones of the target insects, insect extracts containing pheromones, or other non-pheromone compounds known to attract the target insects.

Unless defined otherwise, all technical and scientific terms used herein have the same meaning as commonly understood by one of ordinary skill in the art to which the invention belongs. The term "about" is defined as plus or minus ten percent; for example, about 100° C. means 90° C. to 110° C. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Methods. Strains used were *C. vaccinii* strains MWU205$^T$, MWU205W, MWU300, MWU300W, MWU328, and MWU328W; *C. subtsugae* strain PRAA4-1$^T$ and *B. thuringiensis* strains IBL 10003 (IPS 82 var. *israelensis*; de Barjac, H., and I. Llarget-Thiery, Characteristics of IPS 82 as standard for biological assay of *Bacillus thuringiensis* H-14 preparations, WHO Mimeographed Document, WHO/VBC/84.892, Geneva, Switzerland (1984)) were used as a positive control and IBL 717 (var. *finitimus*) used as a negative control. *C. Vaccinii* Strains with a 'W' ('White') are Pleiotropic Pigment-Deficient Mutants Derived from their cognate wild types.

*Chromobacterium* strains were grown on King's B medium (Atlas, R. M., Handbook of Microbiological Media, 3rd Edition. pp. 876, Boca Raton: CRC Press, Inc. (2004)) at 25° C. for 5 days and *B. thuringiensis* strains were grown on T3 medium (Travers, R. S., et al., Applied and Environmental. Microbiology, 53:1263-1266 (1989)) at 30° C. for 4 days until sporulation. Strains were harvested in 15 mL of distilled water.

*Aedes aegypti* mosquito eggs were obtained from ARS Mosquito and Fly Unit in Gainesville, Fla. Eggs were hatched, fed fish food, and tested 6 days after hatching. 10 mL distilled water was added to 20 mL scintillation vials. Ten mosquito larvae were added to each vial followed by 100 μL of a bacterial suspension. IBL 10003 was used as a positive control of a strain of bacteria known to kill mosquito larvae. Negative controls included a starved control to which no bacteria were added and IBL 717, a strain of bacteria known not to kill mosquito larvae. Vials were incubated at 25° C. and 50% relative humidity in continuous light. Dead larvae were counted at 16 and 72 hours.

Bioassays on diamondback moths were conducted using diamondback moth freeze dried diet (Martin, P. A. W., Biological Control, 29: 109-114 (2004)). Second instar diamondback larvae were used which had been reared at 25° C. with a 16:8 L:D photoperiod and 60% RH. Strains were grown and harvested as described above. Mortality was assayed every 24 h.

Results: Wild type *C. vaccinii* strains MWU300 and MWU328 were surprisingly toxic against mosquito larvae as compared to the negative control Bt IBL 717, and were surprisingly comparable to the 'gold standard' Bti IBL 10003 by 72 h (FIG. 1). Strain MWU205 and *C. subtsugae* PRAA4-1 were somewhat toxic to larvae at 72 h but were not as effective at killing larvae as MWU300 and MWU328. Additionally, PRAA4-1 and MWU205 showed less than 20% mortality at 16 h and less than 60% mortality at 72 h compared to the greater than 80% mortality of MWU300 and 100% mortality of MWU328 at 48 h and 100% mortality at 72 h. Unlike the Bt strains, *C. vaccinii* surprisingly stayed suspended in the water which was easy to observe by the violet color with turbidity (cloudiness). The water in the Bt stains at 16 h was clear, indicating that Bt cells had lysed or settled to the bottom of the vial, away from the larvae. Cognate (i.e., mutants which have arisen from the wild type strain of the same number) violacein-deficient ('White') strains MWU205W, MWU300W and MWU328W had no toxicity against *A. aegypti* mosquitoes after 72 h and the surviving mosquitoes were larger than the starved controls (FIG. 3). MWU205, as in previous experiments, had some activity against *Aedes* larvae but at less than 50% mortality are not considered effective larvacides. PRAA4-1 and MWU205 both produced amounts of the violet pigments violacein and deoxyviolacein that was comparable to MWU300 and MWU328, indicating that MWU300 and MWU328 produced some additional insecticidal toxin which was not produced by the white mutants. These mutants are known to be pleiotropic and have a 'global' regulatory defect. This is important because it indicated that the insecticidal properties of MWU300 and MWU328 were surprisingly due to some component that was not present or was in lower concentrations in other, previously known chromobacteria, such as hydrogen cyanide (FIG. 9) and these insecticidal activities set *C. vaccinii* apart phenotypically from *C. subtsugae* and *C. violaceum*. The *C. vaccinii* strain with the highest toxicity (MWU328) was diluted, and at up to a 1:100 dilution there was still up to 80% mortality relative to Bti IBL 10003 by 72 h (FIG. 4). This indicated insecticidal activity even at relatively low concentrations in water suspension.

Activity against diamondback larvae peaked at 81% for MWU205 at 120 h (FIG. 2). MWU300 also had about 50% mortality at the same time point whereas MWU328 had only 6.3% mortality. There was no mortality in the negative control. Positive control strain *C. subtsugae* PRAA 4-1 had 100% mortality under the same conditions. The white strains, MWU205W and MWU300W, had no detectable mortality, but MWU328W had 37.5% mortality. This is important because white mutant MWU328 produced five times the mortality as its cognate wild type, suggesting that the pleiotropic regulatory mutation that suppresses mosquito larva mortality also increases moth toxicity in this isolate. Once again, these are independent of the purple pigments violacein and deoxyviolacein.

*Chromobacterium* isolates, including the type isolates of *C. violaceum* and *C. subtsugae* were subjected to Matrix-assisted laser desorption/ionization-time of flight mass spectrometry (MALDI-TOF MS), a technique in which a co-precipitate of an UV-light absorbing matrix and bacterial protein extracts are irradiated by a nanosecond laser pulse. The ionized biomolecules were accelerated in an electric field where the molecules were separated according to their mass to charge ratio (m/z) and impacted the detector at different times, yielding a unique signal for each type of bacterium. The technique is useful for bacterial identification and characterization because it reproducibly shows common and unique proteins as peaks for each sample. This proteome sample shows that all three *Chromobacterium* species shared common peaks, indicating that they belong to the same genus, but *C. vaccinii* and *C. violaceum* had shared peaks (green lines) which are absent from *C. subtsugae*, which had peaks that were not present in the other species (red arrows) clearly indicating that they are a different species, with a clearly differing phenotype (FIG. 5). A dendrogram of the MALDI-TOF-MS data constructed using the Unweighted Pair Group Method with Arithmetic Mean (UPGMA) indicated the relationships between *Chromobacterium* species (FIG. 6). The phylogeny of *Chromobacterium* proteomes clearly, and surprisingly indicated that *C. subtsugae* was phenotypically quite different from *C. vaccinii*. Some of the peaks present in *C. vaccinii* wild type strains were not present in the white mutants or in the other chromobacteria (FIG. 7). These proteins may or may not be involved in larvaecidal activity, but are excellent phenotypic markers for wild type *C. vaccinii.*

The 16S rRNA genes of each of the chromobacteria were either cloned and sequenced or accessed through the NCBI database and used to construct a phylogenetic tree by the neighbor-joining method (FIG. 8). This 16S rRNA tree clearly shows that *C. subtsugae* was in a separate Glade from *C. vaccinii*. The placement of other chromobacteria in different clades, and particularly isolates labeled as '*C. violaceum*' indicated that the genus was not stable and will require further taxonomic refinement over time. However, what was immediately clear was that *C. vaccinii, C. subtsugae* and *C. violaceum* were taxonomically independent, had different genotypic and phenotypic characteristics, and had different spectra for insecticidal activity.

Genotypic characterization of *C. vaccinii* isolates by 16S rRNA sequences:

16S rRNA sequence for MWU205 accession number JN120869.1, SEQ ID NO: 1:

```
  1 agagtttgat catggctcag attgaacgct ggcggcatgc tttacacatg caagtcgaac 61 ggtaacaggg tgcttgcacc gctgacgagt ggcgaacggg tgagtaatgc gtcggaatgt 121 accgtgtaat gggggatagc tcggcgaaag ccggattaat accgcatacg ccctgagggg 181 gaaagtgggg gaccgtaagg cctcacgtta tacgagcagc cgacgtctga ttagctagtt 241 ggtgaggtaa gagctcacca aggcgacgat cagtagcggg tctgagagga tgatccgcca
```

-continued

```
 301 cactgggact gagacacggc ccagactcct acgggaggca gcagtgggga attttggaca
 361 atgggcgcaa gcctgatcca gccatgccgc gtgtctgaag aaggccttcg ggttgtaaag
 421 gacttttgtt cgggaggaaa tcccgctggt taatacctgg cggggatgac agtaccggaa
 481 gaataagcac cggctaacta cgtgccagca gccgcggtaa tacgtagggt gcaagcgtta
 541 atcggaatta ctgggcgtaa agcgtgcgca ggcggttgtg caagtttgat ttgaaagccc
 601 cgggcttaac ctgggaacgg cattggagac tgcacgacta gagtgcgtca gaggggggta
 661 gaattccacg tgtagcagtg aaatgcgtag agatgtggag gaataccgat ggcgaaggca
 721 gccccctggg atgacactga cgctcatgca cgaaagcgtg gggagcaaac aggattagat
 781 accctggtag tccacgccct aaacgatgtc aactagctgt tgggggtttg aatccttggt
 841 agcgtagcta acgcgtgaag ttgaccgcct ggggagtacg gccgcaaggt taaaactcaa
 901 aggaattgac ggggacccgc acaagcggtg gatgatgtgg attaattcga tgcaacgcga
 961 aaaaccttac ctgctcttga catgtacgga acttggtaga gatatcttgg tgcccgaaag
1021 ggagccgtaa cacaggtgct gcatggctgt cgtcagctcg tgtcgtgaga tgttgggtta
1081 agtcccgcaa cgagcgcaac ccttgtcatt agttgccatc attaagttgg gcactctaat
1141 gagactgccg gtgacaaacc ggaggaaggt ggggatgacg tcaagtcctc atggccctta
1201 tgagcagggc ttcacacgtc atacaatggt cggtacagag ggttgccaag ccgcgaggtg
1261 gagctaatct cagaaaaccg atcgtagtcc ggatcgcact ctgcaactcg agtgcgtgaa
1321 gtcggaatcg ctagtaatcg cagatcagca tgctgcggtg aatacgttcc cgggtcttgt
1381 acacaccgcc cgtcacacca tgggagtgag tttcaccaga agtgggtagg ctaaccgcaa
1441 ggaggccgct taccacggtg ggattcatga ctggggtgaa gtcgtaacaa ggtagccgta
1501 ggggaacctg cggctggatc acctcctt
```

16S rRNA sequence for MWU328 accession number JN120870.1, SEQ ID NO: 2:

```
   1 agagtttgat catggctcag attgaacgct ggcggcatgc tttacacatg caagtcgaac
  61 ggtaacaggg tgcttgcacc gctgacgagt ggcgaacggg tgagtaatgc gtcggaatgt
 121 accgtgtaat gggggatagc tcggcgaaag ccggattaat accgcatacg ccctgagggg
 181 gaaagtgggg gaccgtaagg cctcacgtta tacgagcagc cgacgtctga ttagctagtt
 241 ggtgaggtaa gagctcacca aggcgacgat cagtagcggg tctgagagga tgatccgcca
 301 cactgggact gagacacggc ccagactcct acgggaggca gcagtgggga attttggaca
 361 atgggcgcaa gcctgatcca gccatgccgc gtgtctgaag aaggccttcg ggttgtaaag
 421 gacttttgtt cgggaggaaa tcccgctggt taatacctgg cggggatgac agtaccggaa
 481 gaataagcac cggctaacta cgtgccagca gccgcggtaa tacgtagggt gcaagcgtta
 541 atcggaatta ctgggcgtaa agcgtgcgca ggcggttgtg caagtctgat gtgaaagccc
 601 cgggcttaac ctgggaacgg cattggagac tgcacgacta gagtgcgtca gaggggggta
 661 gaattccacg tgtagcagtg aaatgcgtag agatgtggag gaataccgat ggcgaaggca
 721 gccccctggg atgacactga cgctcatgca cgaaagcgtg gggagcaaac aggattagat
 781 accctggtag tccacgccct aaacgatgtc aactagctgt tgggggtttg aatccttggt
 841 agcgtagcta acgcgtgaag ttgaccgcct ggggagtacg gccgcaaggt taaaactcaa
 901 aggaattgac ggggacccgc acaagcggtg gatgatgtgg attaattcga tgcaacgcga
 961 aaaaccttac ctgctcttga catgtacgga acttggtaga gatatcttgg tgcccgaaag
```

```
1021 ggagccgtaa cacaggtgct gcatggctgt cgtcagctcg tgtcgtgaga tgttgggtta 1081 agtcccgcaa cgagcgcaac ccttgtcatt agttgccatc attaagttgg cactctaat 1141 gagactgccg gtgacaaacc ggaggaaggt ggggatgacg tcaagtcctc atggccctta

1201 tgagcagggc ttcacacgtc atacagtggt cggtacagag ggttgccaag ccgcgaggtg 1261 gagctaatct cagaaaaccg atcgtagtcc ggatcgcact ctgcaactcg agtgcgtgaa 1321 gtcggaatcg ctagtaatcg cagatcagca tgctgcggtg aatacgttcc cgggtcttgt 1381 acacaccgcc cgtcacacca tgggagtgag tttcaccaga agtgggtagg ctaaccgcaa 1441 ggaggccgct taccacggtg ggattcatga ctggggtgaa gtcgtaacaa ggtagccgta 1501 ggggaacctg cggctggatc acctcctt
```

16S rRNA sequence for MWU300 accession number JN117594, SEQ ID NO: 3:

```
  1 agagtttgat catggctcag attgaacgct ggcggcatgc tttacacatg caagtcgaac 61 ggtaacaggg tgcttgcacc gctgacgagt ggcgaacggg tgagtaatgc gtcggaatgt 121 accgtgtaat gggggatagc tcggcgaaag ccggattaat accgcatacg ccctgagggg 181 gaaagtgggg gaccgtaagg cctcacgtta tacgagcagc cgacgtctga ttagctagtt 241 ggtgaggtaa gagctcacca aggcgacgat cagtagcggg tctgagagga tgatccgcca 301 cactgggact gagacacggc ccagactcct acgggaggca gcagtgggga attttggaca 361 atgggcgcaa gcctgatcca gccatgccgc gtgtctgaag aaggccttcg ggttgtaaag 421 gacttttgtt cggaggaaa tcccgctggt taatacctgg cggggatgac agtaccggaa 481 gaataagcac cggctaacta cgtgccagca gccgcggtaa tacgtagggt gcaagcgtta 541 atcggaatta ctgggcgtaa agcgtgcgca ggcggttgtg taagtctgat gtgaaagccc 601 cgggcttaac ctgggaacgg cattggagac tgcacgacta gagtgcgtca gagggggta 661 gaattccacg tgtagcagtg aaatgcgtag agatgtggag gaataccgat ggcgaaggag 721 cccctggga tgacactgac gctcatgcac gaaagcgtgg ggagcaaaca ggattagata 781 ccctggtagt ccacgcccta aacgatgtca actagctgtt gggggtttga atccttggta 841 gcgtagctaa cgcgtgaagt tgaccgcctg gggagtacgg ccgcaaggtt aaaactcaaa 901 ggaattgacg gggacccgca caagcggtgg atgatgtgga ttaattcgat gcaacgcgaa 961 aatccttacc tgctcttgac atgtacggaa cttggtagag atatcttggt gcccgaaagg 1021 gagccgtaac acaggctg catggctgtc gtcagctcgt gtcgtgagat gttgggttaa 1081 gtcccgcaac gagcgcaacc cttgtcatta gttgccatca ttaagttggg cactctaatg 1141 agactgccgg tgacaaaccg gaggaaggtg gggatgacgt caagtcctca tggcccttat 1201 gagcagggct tcacacgtca tacaatggtc ggtacagagg gttgccaagc cgcgaggtgg 1261 agctaatctc agaaaaccga tcgtagtccg gatcgcactc tgcaactcga gtgcgtgaag 1321 tcggaatcgc tagtaatcgc agatcagcat gctgcggtga atacgttccc gggtcttgta 1381 cacaccgccc gtcacaccat gggagtgagt tcaccagaa gtgggtaggc taaccgcaag 1441 gaggccgctt accacggtgg gattcatgac tggggtgaag tcgtaacaag gtagccgtag 1501 gggaacctgc ggctggatca cctcctt
```

Figure 9:
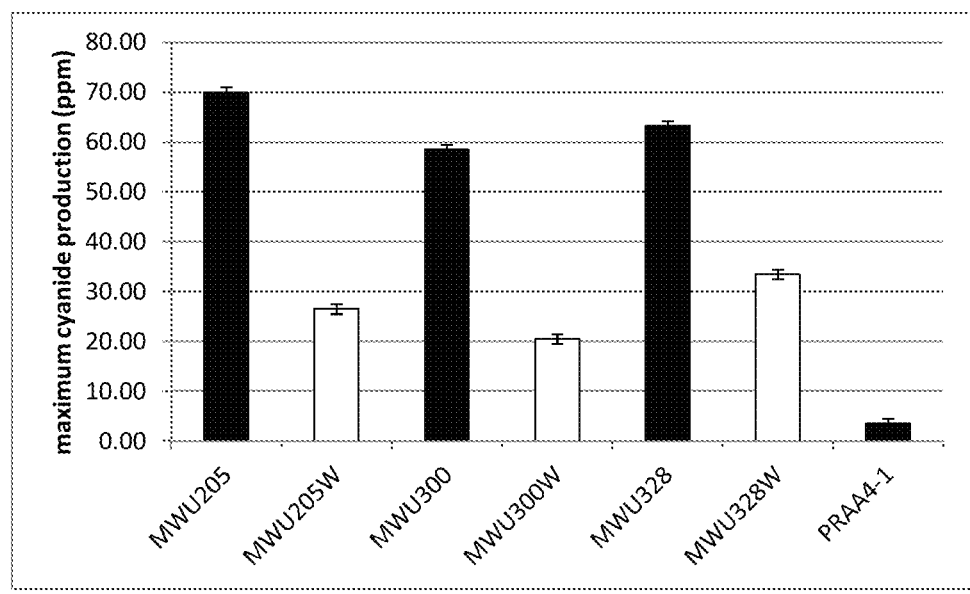
FIG. 9 shows maximum hydrogen cyanide concentrations produced by *C. vaccinii* isolates, cognate non-pigmented mutants, and *C. subtsugae* PRAA4-1 as described below.

Hydrogen cyanide production: Hydrogen cyanide concentrations were determined in 1 mL culture supernatants at pH≥11 by the addition of 100 μL 1N NaOH, and directly measured using a cyanide probe (Lazar Research Laboratories Inc.) attached to a pH meter (Corning Inc. Corning, N.Y.) using a method modified from Zlosnik and Williams (Zlosnik, J. E., and H. D. Williams, Lett. Appl. Microbiol., 38(5): 360-536 (2004)). Direct measurements (mV) were converted to concentration (ppm) by comparison with a standard curve ($R^2$>0.99). Culture densities were standardized by comparison with a standard curve derived from a comparison of $OD_{600}$ with direct colony counts. All experiments were performed at least three times with up to four replicates each. Wild type *C. vaccinii* produced maximum hydrogen cyanide concentrations between seventeen and nineteen hours post inoculation in KMB broth cultures. Production of cyanide was thus assayed by sampling at the eighteen hour post inoculation time point. Surprisingly strain MWU 205 produced the highest HCN concentrations (70 ppm), followed by MWU 328 (62 ppm) and MWU 300 (58 ppm) and each of the non-pigmented mutants produced half or less of the HCN as their cognate wild type isolates. *C. subtsugae* did not produce hydrogen cyanide above background levels (FIG. 9).

Discussion: After the discovery of a new species of *Chromobacterium, C. vaccinii* (Soby, S. D. et al., *Chromobacterium vaccinii* sp. nov. isolated from native and cultivated cranberry (*Vaccinium macrocarpon* Ait.) bogs and irrigation ponds. International Journal of Systematic and Evolutionary Microbiology, ijs.0.045161-0, 2012), we tested it against insects that were killed (e.g. moth larvae) or not killed (e.g. mosquito larvae) by *C. subtsugae*. We also tested *Bacillus thuringiensis* strains and several strains of *C. vaccinii* against *Aedes aeygpti* mosquitoe larvae. It was surprising that there were differences in mosquitocidal activity independent of violacein and deoxyviolacein pigment formation (a secondary metabolite), but dependent on the individual strain. Two of the six strains (MWU300 and MWU328) killed more than 90% of the mosquito larvae in the test by 16 h, which was comparable to the lethality of *B. thuringiensis israelensis*. It is expected that these strains will also kill other mosquito genera as well as other Diptera. One strain, MWU205, had activity against diamondback moth, but was only partially active against *Aedes*.

All of the references cited herein, including U.S. Patents, are incorporated by reference in their entirety. Also incorporated by reference in their entirety are the following references: U.S. Patent Publication 20120100236; de Barjac, H. and I. Llarget-Thiery, Characteristics of IPS 82 a s standard for biological assay of *Bacillus thuringiensis* H-14 preparations, WHO Mimeographed Document, WHO/VBC/84.892, 1984 Geneva, Switzerland; Duran, N., and C. F. Menck, Critical Reviews in Microbiology, 27: 201-222 (2001); Goldberg, L. J., and J. Margalit, Journal of the American Mosquito Control Association 37, 355-358 (1977); Martin, P. A. W., and M. B. Blackburn, Biopesticide International, 4: 102-109 (2008); Soby, S. D., et al., *Chromobacterium vaccinii* sp. nov. isolated from native and cultivated cranberry (*Vaccinium macrocarpon* Ait.) bogs and irrigation ponds, International Journal of Systematic and Evolutionary Microbiology, ijs.0.045161-0 (2012); Yang, C. H., and Y. H. Li, Journal of the Chinese Medical Association 74(10), 435-441 (2011).

Thus, in view of the above, there is described (in part) the following:

A biologically pure culture of *Chromobacterium vaccinii* having all of the identifying characteristics of *C. vaccinii* strains MWU205, MWU300 or MWU328.

The above biologically pure culture of *Chromobacterium vaccinii* strain MWU205, wherein said identifying characteristics include cells are Gram-negative, aerobic, rod-shaped with mean dimensions (mean±sd) of 3.03 µm±0.555×1.19 µm±0.0198; a single polar flagellum having a length of 4.91 µm±0.730; colonies grow on KMB and LB media; resistant to penicillin and ampicillin at 50 µg ml$^{-1}$; optimum growth occurs at 25°-26° C. with growth up to 43° C. on KMB media producing round, smooth, glossy, convex colonies within 48 h starting out as cream-colored and turning purple starting from the center of the colony; violacein and deoxyviolacein production is less at 37° C. than at 25° C. and is absent at 43° C.; produces violacein-deficient mutants when grown on 3% (w/v) NaCl salt concentration media; cells grow freely in 2% (w/v) NaCl, and marginally in 3% (w/v) NaCl; major fatty acids are $C_{16:1}\omega 7cis$ (41.94%), $C_{16:0}$ (29.56%) and $C_{18:0\omega 7cis}$ (12.63%); colonies do not fluoresce under [short or long wave] UV irradiation; produce a water-soluble brown pigment which diffuses freely in the medium; positive for catalase and oxidase; produces arginine dihydrolase and β-galactosidase; assimilates D-glucose, N-acetylglucosamine, gluconate, citrate, capric acid and malic acid; is negative for glucose fermentation, urease and β-glucosidase; does not produce indole from tryptophan; does not assimilate L-arabinose, D-mannitol, maltose or phenylacetic acid; secretes about $7.9 \times 10^{-6}$ ng violacein per cell and produces $1.3 \times 10^{-6}$ ng intracellular violacein per cell when grown on KMB media with aeration; kills diamondback moth larvae but not mosquito larvae at about 16 h post insect hatch.

The above biologically pure culture of *Chromobacterium vaccinii* strain MWU 300, wherein said identifying characteristics include cells are Gram-negative, aerobic, rod-shaped with mean dimensions (mean±sd) of 3.03 µm±0.555×1.19 µm±0.0198; a single polar flagellum having a length of 4.91 µm±0.730; colonies grow on KMB and LB media; are resistant to penicillin and ampicillin at 50 µg ml$^{-1}$; optimum growth occurs at 25°-26° C. with growth up to 43° C. on KMB media producing round, smooth, glossy, convex colonies within 48 h starting out as cream-colored and turning purple starting from the center of the colony; violacein production is less at 37° C. than at 25° C. and is absent at 43° C.; produces violacein-deficient mutants when grown on 3% (w/v) NaCl salt concentration media; cells grow freely in 2% (w/v) NaCl and marginally in 3% (w/v) NaCl; major fatty acids are $C_{16:1\omega 7cis}$ (42.72%), $C_{16:0}$ (28.40%) and $C_{18:1\omega 7cis}$ (13.11%); colonies do not fluoresce under UV irradiation but produce the pigments violacein and deoxyviolacein at up to 37° C. and also producing a water-soluble brown pigment which diffuses freely in the medium; positive for catalase and oxidase; produces arginine dihydrolase and β-galactosidase; assimilates D-glucose, N-acetylglucosamine, gluconate, citrate, capric acid and malic acid, is negative for glucose fermentation, urease and β-glucosidase; does not produce indole from tryptophan or assimilate L-arabinose, D-mannitol, maltose or phenylacetic acid; secretes about $3.4 \times 10^{-6}$ ng violacein per cell and $6.4 \times 10^{-7}$ ng intracellular violacein per cell when grown on KMB media with aeration; and kills mosquito larvae but not diamondback moth larvae.

The above biologically pure culture of *Chromobacterium vaccinii* strain MWU328, wherein said identifying characteristics include cells are Gram-negative, aerobic, rod-shaped with mean dimensions (mean±sd) of 3.03 µm±0.555×1.19 µm±0.0198 (2.01 to 3.91 µm×0.96 to 1.78 µm), a single polar flagellum having a length of 4.91 µm±0.730, colonies grow on KMB and LB media, are resistant to penicillin and ampicillin at 50 µg ml$^{-1}$, optimum growth occurs at 25°-26° C., growing up to 43° C. on KMB media, producing round, smooth, glossy, convex colonies within 48 h, starting out as cream-colored and turning purple starting from the center of the colony, violacein production is less at 37° C. than at 25° C. and is absent at 43° C., produces violacein-deficient mutants when grown on 3% (w/v) NaCl media, cells grow freely in 2% (w/v) NaCl, and marginally in 3% (w/v) NaCl; colonies do not fluoresce under UV irradiation, but produce large amounts of the pigments violacein and deoxyviolacein at up to 37° C., also producing a water-soluble brown pigment which diffuses freely in the medium; positive for catalase and oxidase, produces arginine dihydrolase and β-galactosidase, and assimilates D-glucose, N-acetylglucosamine, gluconate, citrate, capric acid and malic acid, is negative for glucose fermentation, urease and β-glucosidase, does not produce indole from tryptophan; does not assimilate L-arabinose, D-mannitol, maltose or phenylacetic acid; secretes about $2.5 \times 10^{-6}$ ng violacein per cell and produces $4.4 \times 10^{-7}$ ng intracellular violacein per cell when grown on KMB with aeration; kills mosquito larvae but not diamondback moth larvae.

A biologically pure culture of *Chromobacterium vaccinii* MWU205 which has the 16S rRNA gene sequence (NCBI accession number JN120869.1, SEQ ID NO: 1) or a biologically pure culture of *Chromobacterium vaccinii* MWU328 which has the 16S rRNA gene (NCBI accession number JN20870, SEQ ID NO: 2) or a biologically pure culture of *Chromobacterium vaccinii* MWU300 which has the 16S rRNA gene sequence (NCBI accession number JN117594, SEQ ID NO: 3).

A composition useful for control of insect pests, which comprises (or consists essentially of or consists of) the above strain, and optionally a carrier.

A method for killing insects, comprising treating an object or area with an insect killing effective amount of a composition comprising the above strain, and optionally a carrier.

An isolated biologically pure culture of a bacteria strain selected from the group consisting of *Chromobacterium vaccinii* strain MWU205, MWU300, MWU328, and mixtures thereof.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

*Chromobacterium* phenotypes[1]

| Isolate | NO$_3$ reduction | Mannose assimilation | Growth, pH range | Growth temperature range (° C.)[2] | Violacein production temperature range (° C.) | Growth, maximum salinity (%)[3] | Violacein production, maximum salinity (%)[3] |
|---|---|---|---|---|---|---|---|
| MWU205[T] | + | +/− | 5.5[5]-8.5 | 25-43 | 25-37 | 3 | 2[4] |
| MWU300 | + | +/− | 5.5[5]-8.5 | 25-43 | 25-37 | 3[4] | 2[4] |
| MWU328 | + | +/− | 5.5[5]-8.5 | 25-43 | 25-37 | 3 | 2[4] |
| C. subtsugae PRAA4-1[T] | − | − | 5.5-8.5 | 26-37 | 26-37 | 1 | 1 |
| C. violaceum ATCC12472[T] | + | + | 5.5-8.5 | 26-45 | 26-45 | 2 | 2 |

[1]No differences were detected among strains for oxidase, catalase, motility, indole production, glucose fermentation, arginine dihydrolase, gelatinase, urease, β-glucosidase, β-galactosidase, and assimilation of D-glucose, L-arabinose, D-mannitol, N-acetyl-glucosamine, maltose, gluconate, capric acid, adipic acid, malic acid, citrate, or phenyl-acetic acid.
[2]Growth and violacein production were tested at 4, 26, 37, 43 and 45° C. on King's Medium B
[3]Salt tolerance was determined by growth at 26° C. on LB agar supplemented with NaCl. Total concentrations are shown.
[4]Reduced compared to LB (1% NaCl)
[5]Slow and reduced

We claim:

1. A method for killing insects, comprising treating an object or area with an insect killing effective amount of a composition comprising biologically pure culture of *Chromobacterium vaccinii* having all of the identifying characteristics of *C. vaccinii* strains MWU205, MWU300 or MWU328, and optionally a carrier.

2. The method according to claim 1, wherein said biologically pure culture of *Chromobacterium vaccinii* is strain MWU205, wherein said identifying characteristics include cells are Gram-negative, aerobic, rod-shaped with mean dimensions (mean±sd) of 3.03 µm±0.555×1.19 µm+0.0198; a single polar flagellum having a length of 4.91 µm±0.730; colonies grow on KMB and LB media; resistant to penicillin and ampicillin at 50 µg ml$^{-1}$; optimum growth occurs at 25-26° C. with growth up to 43° C. on KMB media producing round, smooth, glossy, convex colonies within 48 h starting out as cream-colored and turning purple starting from the center of the colony; violacein production is less at 37° C. than at 25° C. and is absent at 43° C.; produces violacein-deficient mutants when grown on 3% (w/v) NaCl salt concentration media; cells grow freely in 2% (w/v) NaCl, and marginally in 3% (w/v) NaCl; major fatty acids are $C_{16:1\omega7cis}$ in an amount of 41.94%, $C_{16:0}$ in an amount of 29.56% and $C_{18:1\omega7cis}$ in an amount of 12.63%; colonies do not fluoresce under UV irradiation; produce pigments violacein and deoxyviolacein at up to 37° C.; produce a water-soluble brown pigment which diffuses freely in the medium; produces a maximum concentration of about 70 ppm hydrogen cyanide in planktonic culture; positive for catalase and oxidase; produces arginine dihydrolase and β-galactosidase; assimilates D-glucose, N-acetylglucosamine, gluconate, citrate, capric acid and malic acid; is negative for glucose fermentation, urease and β-glucosidase; does not produce indole from tryptophan; does not assimilate L-arabinose, D-mannitol, maltose or phenylacetic acid; secretes about $7.9\times10^{-6}$ ng violacein per cell and produces $1.3\times10^{-6}$ ng intracellular violacein per cell when grown on KMB media with aeration; kills diamondback moth larvae but not mosquito larvae at about 16 h post insect hatch.

3. The method according to claim 1, wherein said biologically pure culture of *Chromobacterium vaccinii* is strain MWU 300, wherein said identifying characteristics include cells are Gram-negative, aerobic, rod-shaped with mean dimensions (mean±sd) of 3.03 µm±0.555×1.19 µm±0.0198; a single polar flagellum having a length of 4.91 µm±0.730; colonies grow on KMB and LB media; are resistant to penicillin and ampicillin at 50 µg ml$^{-1}$; optimum growth occurs at 25-26° C. with growth up to 43° C. on KMB media producing round, smooth, glossy, convex colonies within 48 h starting out as cream-colored and turning purple starting from the center of the colony; violacein production is less at 37° C. than at 25° C. and is absent at 43° C.; produces violacein-deficient mutants when grown on 3% (w/v) NaCl salt concentration media; cells grow freely in 2% (w/v) NaCl and marginally in 3% (w/v) NaCl; major fatty acids are $C_{16:1\omega7cis}$ in an amount of 42.72%, $C_{16:0}$ in an amount of 28.40% and $C_{18:1\omega7cis}$ in an amount of 13.11%; colonies do not fluoresce under UV irradiation but produce the pigments violacein and deoxyviolacein at up to 37° C. and also produce a water-soluble brown pigment which diffuses freely in the medium; produces a maximum concentration of about 58 ppm hydrogen cyanide in planktonic culture; positive for catalase and oxidase; produces arginine dihydrolase and β-galactosidase; assimilates D-glucose, N-acetylglucosamine, gluconate, citrate, capric acid and malic acid, is negative for glucose fermentation, urease and β-glucosidase; does not produce indole from tryptophan or assimilate L-arabinose, D-mannitol, maltose or phenylacetic acid; secretes about $3.4\times10^{-6}$ ng violacein per cell and $6.4\times10^{-7}$ ng intracellular violacein per cell when grown on KMB media with aeration; and kills mosquito larvae but not diamondback moth larvae.

4. The method according to claim 1, wherein said biologically pure culture of *Chromobacterium vaccinii* is strain MWU328, wherein said identifying characteristics include cells are Gram-negative, aerobic, rod-shaped with mean dimensions (mean±sd) of 3.03 µm 0.555×1.19 µm±0.0198 (2.01 to 3.91 µm×0.96 to 1.78 µm), a single polar flagellum having a length of 4.91 µm±0.730, colonies grow on KMB and LB media, are resistant to penicillin and ampicillin at 50 µg ml$^{-1}$, optimum growth occurs at 25-26° C., growing up to 43° C. on KMB media, producing round, smooth, glossy, convex colonies within 48 h, starting out as cream-colored and turning purple starting from the center of the colony, violaccin production is less at 37° C. than at 25° C. and is absent at 43° C., produces violacein-deficient mutants when grown on 3% (w/v) NaCl media, cells grow freely in 2% (w/v) NaCl, and marginally in 3% (w/v) NaCl; colonies do not fluoresce under UV irradiation, but produce large amounts of the pigments violacein and deoxyviolacein at up to 37° C., also producing a water-soluble brown pigment which diffuses freely in the medium; produces a maximum concentration of about 63 ppm hydrogen cyanide in planktonic culture; positive for catalase and oxidase, produces arginine dihydrolase and β-galactosidase, and assimilates D-glucose, N-acetylglucosamine, gluconate, citrate, capric acid and malic acid, is negative for glucose fermentation, urease and β-glucosidase, does not produce indole from tryptophan; does not assimilate L-arabinose, D-mannitol, maltose or phenylacetic acid; secretes about $2.5\times10^{-6}$ ng violaccin per cell and produces $4.4\times10^{-7}$ ng intracellular violacein per cell when grown on KMB with aeration; kills mosquito larvae but not diamondback moth larvae.

5. The method according to claim 1, wherein said strain MWU205 has the 16S rRNA gene sequence SEQ ID NO: 1, wherein said strain MWU300 has the 16S rRNA gene sequence SEQ ID NO: 3, wherein said strain MWU328 has the 16S rRNA gene SEQ ID NO: 2.

* * * * *